(12) United States Patent
DiMauro et al.

(10) Patent No.: US 7,673,634 B2
(45) Date of Patent: Mar. 9, 2010

(54) METHOD OF TREATING OR PREVENTING OSTEOLYSIS IN A PATIENT BY UVB LIGHT IRRADIATION

(75) Inventors: Thomas M. DiMauro, Southboro, MA (US); Mohamed Attawia, Canton, MA (US); Chantal Holy, Somerville, MA (US); Hugo Pedrozo, Austin, TX (US); Jeffrey K. Sutton, Medway, MA (US)

(73) Assignee: Depuy Spine, Inc, Raynham, MA (US)

( * ) Notice: Subject to any disclaimer, the term of this patent is extended or adjusted under 35 U.S.C. 154(b) by 1174 days.

(21) Appl. No.: 11/235,460

(22) Filed: Sep. 26, 2005

(65) Prior Publication Data

US 2006/0111291 A1    May 25, 2006

Related U.S. Application Data

(60) Provisional application No. 60/617,332, filed on Oct. 8, 2004.

(51) Int. Cl.
    *A61B 19/00* (2006.01)
(52) U.S. Cl. .......................................... 128/898; 607/88
(58) Field of Classification Search ............. 607/88–95; 128/898; 606/3, 8–12, 53
    See application file for complete search history.

(56) References Cited

U.S. PATENT DOCUMENTS

| 5,282,864 | A | 2/1994 | Noiles et al. |
|---|---|---|---|
| 5,733,545 | A | 3/1998 | Hood, III |
| 5,910,309 | A | 6/1999 | Ullrich |
| 5,935,577 | A | 8/1999 | Weiner et al. |
| 6,017,975 | A | 1/2000 | Saum et al. |
| 6,083,919 | A | 7/2000 | Johnson et al. |
| 6,214,049 | B1 | 4/2001 | Gayer et al. |
| 6,228,900 | B1 | 5/2001 | Shen et al. |
| 6,645,504 | B1 | 11/2003 | Weiner et al. |
| 6,964,667 | B2 * | 11/2005 | Shaolian et al. ............... 606/99 |
| 7,229,467 | B2 * | 6/2007 | Spivak ........................ 607/88 |
| 7,353,830 | B2 * | 4/2008 | Lee et al. .................... 128/898 |
| 2002/0198526 | A1 * | 12/2002 | Shaolian et al. ............... 606/61 |

FOREIGN PATENT DOCUMENTS

| EP | 1346752 A2 | 9/2003 |
|---|---|---|
| WO | 9729793 A1 | 8/1997 |
| WO | 9946742 A1 | 9/1999 |

OTHER PUBLICATIONS

Simon et al., Skin Pharmacol Appl Skin Physiol., *UVB-Irradiated Dendritic Cells Induce Nonproliferating, Regulatory Type T Cells*, 15, 2002, pp. 330-334.
Anderson, C. et al., J. of Immunology, *Cutting Edge: Biasing Immune Responses by Directing Antigen to Marcophage Fcy Receptors*, 168, 2002, pp. 3697-3701.
Anderson, C. et al., J. Endotoxin Research, *Modulating Macrophage Function with IgG Immune Complexes*, 8(6), 2002, pp. 477-481.
Arora, A. et al., JBMA, *The Role of the TH1 and TH2 Immune Responses in Loosening and Osteolysis of Cemented Total Hip Replacements*, 64A, 2003, pp. 693-697.

(Continued)

*Primary Examiner*—Ahmed M Farah

(57) ABSTRACT

Irradiating osteolytic regions with UVB light.

15 Claims, 2 Drawing Sheets

OTHER PUBLICATIONS

Bosetti, M. et al., Biomaterials, *In Vitro Evaluation of the Inflammatory Activity of Ultra-high Molecular Weight Polyethylene*, 24(8), 2003, pp. 1419-1426.

Brennen, F., Rheumatology, *Interleukin 10 and Arthritis*, 38, 1999, pp. 293-297.

Carmody, E. et al., Arthritis & Rheumatism, *Viral Interleukin-10 Gene Inhibition of Inflammation, Osteoclastogenesis, and Bone Resorption in Response to Titanium Particles*, 46(5), 2002, pp. 1298-1308.

Chen, Y. et al., Science, *Regulatory T Cell Clones Induced by Oral Tolerance: Suppression of Autoimmune Encephalomyelitis*, 265, 1994, pp. 1237-1240.

Goodman, S. et al., JBMR, *Modulation of Bone Ingrowth and Tissue Differentiation . . .* , 65A, 2003, pp. 43-50.

Hart, P. et al., Immunology, *Comparison of the Suppressive Effects of Interleukin-10 and interleukin-4 on Synovial Fluid Marcophages . . .* , 84(4), 1995, pp. 536-542.

Kang, K. et al., J. Immunology, *CD11b+ Marcophages that Infiltrate Human Epidermis after In Vivo Ultraviolet Exposure . . .* , 153, 1994, pp. 5256-5264.

King, C. et al., Immunity, *TGF-β1 Alters APC Preference, Polarizing Islet Antigen Responses Toward a Th2 Phenotype*, 8, 1998, pp. 601-613.

Kossovsky, N. et al., CRC Critical Reviews in Biocompatibility, *The Bioreactivity of Silicone*, 3(1), 1987, pp. 53-85.

Liu, Y. et al., Nature Immunology, *Dendritic Cell Lineage, Plasticity and Cross-regulation*, 2(7), 2001, pp. 585-589.

Ossevoort, M. et al., J. Immunological Methods, *A Rapid Isolation Procedure for Dendritic Cells from Mouse Spleen by Centrifugal Elutriation*, 155(1), 1992, pp. 101-111.

Pollice, P. et al., J. Orthrop. Research, *Interleukin-10 Inhibits Cytokine Synthesis in Monocytes Stimulated by Titanium Particles . . .* , 16(6), 1998, pp. 697-704.

Rivas, J. et al., J. Immunology, *Systemic Suppression of Delayed-Type Hypersensitivity . . .* , 149(12), 1992, pp. 3865-3871.

Schmitt, D. et al., J. Immunology, *Exposure to Ultraviolet Radiation Causes Dendritic Cells/Macrophages to Secrete Immune-suppressive IL-12p40 Homodimers*, 165, 2000, pp. 3162-3167.

Shreedhar, V. et al., J. Immunology, *A Cytokine Cascade Including Prostaglandis $E_2$, IL-4, and IL-10 . . .* , 160, 1998, pp. 3783-3789.

Stuart, J. et al., J. Exp. Med., *Type II Collagen-Induced Arthritis in Rats*, 155, 1982, pp. 1-16.

Stutzmann, M., et al., Diamond & Related Materials, *GaN-based Heterostructures for Sensor Applications*, 11, 2002, pp. 886-891.

Trindade, M. et al., Biomaterials 22, *Interleukin-10 Inhibits Polymethylmethacrylate Particle Induced Interleukin-6 and Tumor Necrosis . . .* , 2001, pp. 2067-2073.

Virri, J. et al., Spine, *Comparison of the Prevalence of Inflammatory Cells in Subtypes of Disc Herniations and Associations with Straight Leg Raising*, 26(21), 2001, pp. 2311-2315.

Wooley, P. et al., JBJS, *Proteins Bound to Polyethylene Components in Patients who have Aseptic Loosening after Total Joint Arthroplasty*, 81A(5), 1999, pp. 616-623.

\* cited by examiner

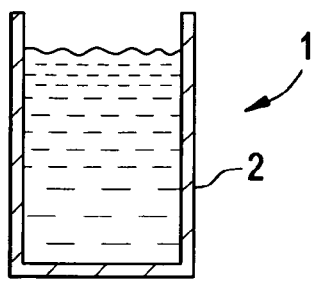
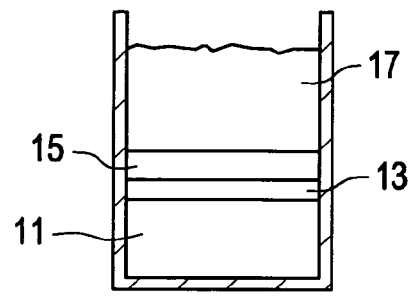
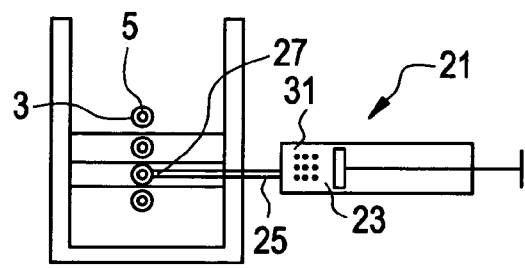
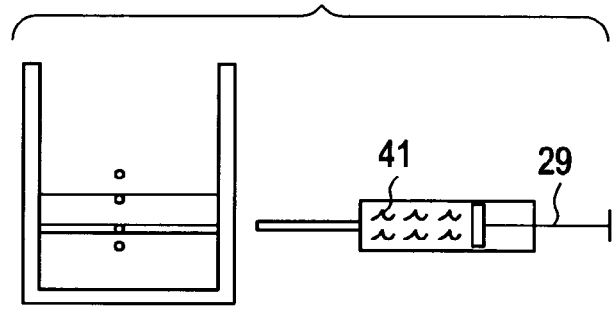
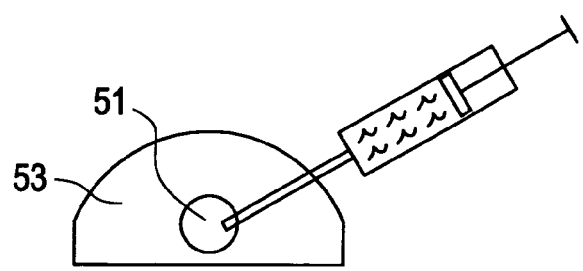

METHOD OF TREATING OR PREVENTING OSTEOLYSIS IN A PATIENT BY UVB LIGHT IRRADIATION

CONTINUING DATA

This application claims priority from U.S. Provisional Patent Application No. 60/617,332, entitled "UV Device for Treating Osteolysis" (DiMauro), filed Oct. 8, 2004.

BACKGROUND OF THE INVENTION

Minute particles emanating from either ultra high molecular weight polyethylene ("UHMWPE") interfaces or polymethylmethacrylate ("PMMA") cement cause an inflammatory immune response resulting in osteolysis (i.e., dissolution or degeneration of bone tissue). Osteolysis is believed to be a primary causes of implant revision in hip and knee implants. It is believed the method of the present invention is applicable to other implants that are susceptible to the above-described mechanism of inflammatory immune response resulting in osteolysis including other artificial joints such as spinal discs.

Conventional means of treating osteolysis include: a) providing smoother wear surfaces; b) providing more wear resistant UHMWPE; c) a continuous infusion pump or gene technology as a means of providing IL-10; and d) prosthetic revision surgery.

Some of the osteolysis literature has suggested that the complexing of polyethylene and IgG leads to a Th1-type pro-inflammatory response. It has been suggested in the literature that certain implanted polymers such as silicone may provide an adjuvant-like activity to native macromolecules, which adhere to hydrophobic surfaces and subsequently become immunogenic. Kossovsky, *CRC Crit. Rev. Biocompat.* 3, 53-85, 1987. In regards to UWMWPE, Wooley, *JBJS*, 81-a (5) May 1999, 616-623, has suggested that most hip joint prosthesis patients express antibodies that are reactive with the proteins bound to polyethylene and that type I collagen is a major antigenic target in these patients. Wooley reported that type I collagen was often found bound to polyethylene particles, and further suggested that the implantation of the biomaterial, followed by deposition of collagen, may contribute to increased levels of antibodies. Wooley then hypothesizes that immunoglobulin complexed with polyethylene may fix complement and that the complement cascade may in turn attract inflammatory cells to the polyethylene surface. Stuart, *J. Exp. Med.*, 155, January 1982, 1-16, reports that IgG anticollagen antibodies can cause arthritis. Bosetti, *Biomaterials*, 24, 2003, 1419-26 reports the adsorption of pro-inflammatory IgG upon the surface of UHMWPE.

Accordingly, the literature suggested not only that the binding of collagen to polyethylene but also the binding of IgG to polyethylene may drive a pro-inflammatory response.

Another portion of the osteolysis literature has suggested that the complexation of polyethylene and IgG leads to a Th2-type anti-inflammatory response. For example, Anderson, *J. Imunology*, 2002, 168:3697-3701, ("Anderson I") reports that whereas use of macrophages as antigen-presenting cells (APCs) resulted in a strong polarized T cell response predominated by Th1 cytokines, when the antigen was targeted to $FC\chi$ receptors on these APCs, the T cell response was reversed and biased toward a Th2-type response. Anderson I concludes that when APCs encounter immune complexes, their cytokine production is modulated to create a cytokine microenvironment which preferentially induces a Th2-like response dominated by IL-4, and that IgG can override innate signals generated by microbial products and drive Th2-like immune responses. Anderson, *J. Endotoxin Research* 8(6), 2002, 477-481, ("Anderson II") reports that cells exposed to IgG immune complexes generate large amounts of IL-10, and as a result exert a potent anti-inflammatory effect on the immune response. Anderson II further reports that the ligation of $FC\chi$ receptors on activated macrophages by antigen—IgG complexes induced T cells to produce IL-4, which in turn induced B cells to produce IgG1 (a Th2 IgG) in response to that antigen. Anderson II concludes that the mechanism by which IgG can influence immune deviation is by changing the phenotype of the APC, inducing the production of IL-10 instead of IL-12.

Accordingly, the literature suggests that the production of UHMWPE wear debris may drive both Th1 and Th2 responses. The suggestion of a mixed response is consistent with the reporting of Arora, *JBMR* 64A: 693-697, 2003. Arora examined the specific role of lymphocytes in the Th1 and Th2 subsets in osteolysis and aseptic loosening and found significant numbers of T cells and Th1 and Th2 immune cytokines, and concluded there was a possibility of an immune response at the prosthetic interface.

Since it is likely that the production of UHMWPE wear debris invokes a mixed type immune response involving both Th1 and Th2 cells and both pro- and anti-inflammatory cytokines, the present inventors believe that the presence of a significant Th1 component in the immune response is responsible for the induction of osteolysis.

There have been a number of reports disclosing the beneficial effects of IL-10 upon osteolysis. For example, Pollice *J. Orthop. Res.* 1998 November 16(6) 697-704 discloses that IL-10 inhibits inflammatory cytokine synthesis by monocytes stimulated with titanium particles. Trindade, *Biomaterials* 22(2001) 2067-73 discloses that IL-10 inhibits PMMA induced IL-6 and TNF-a release by human monocytes/macrophages in vitro. Goodman, *JBMR*, 65A:43-50, 2003 used a small infusion pump to continuously provide IL-10 to a site contaminated with UHMWPE particles and found that local infusion of immune-modulating cytokines such as IL-10 may prove to be useful in abating particle-induced periprosthetic osteolysis. Carmody, *Arthritis & Rheumatism*, 46(5) May 2002 pp. 1298-1308 teaches viral IL-10 gene inhibition of inflammation, osteoclastogenesis and bone resorption in response to titanium particles.

It is an object of the present invention to treat osteolysis resulting from orthopedic implants so that revision surgery is not needed or is significantly delayed.

SUMMARY OF THE INVENTION

The present invention relates to an improved orthopedic implant or probe having an ultraviolet B (UVB) light. The UVB light irradiation of the osteolytic region causes macrophages participating in the inflammatory response to emit anti-inflammatory cytokines such as IL-4 and IL-10.

Thus, whereas the prior art methods of abating osteolysis require either a continuous infusion pump or gene technology as a means of providing IL-10, the present invention does so by an implanted UVB device or by a UVB probe.

Without wishing to be tied to a theory, it is further believed that UVB light may also be effective in activating the Th2 pathway in local cells and inactivating the Th1 pathway. Because the Th2 pathway is considered to be anti-inflammatory while the Th1 pathway is considered to be pro-inflammatory, the effect of UVB light may be that of immunosuppression. This quality may help attenuate osteolysis.

The implants of present invention can be activated by the patient on a routine or as-needed basis.

DESCRIPTION OF THE FIGURES

FIG. 2 is a cross-section of a centrifugation container filled with whole blood.

FIG. 3 is a cross-section of a centrifugation container filled with centrifuged blood.

FIG. 4 is a side view of a syringe filled with collagen—Wear Particle complexes having a needle inserted into the container of FIG. 3.

FIG. 5 is a side view of the syringe of FIG. 3 having a UVB-producing unit attached thereto.

FIG. 6 is a cross-section of a syringe of the present invention injecting tolerized white blood cells into the vicinity of a lymph node.

DETAILED DESCRIPTION OF THE INVENTION

Figure 1:
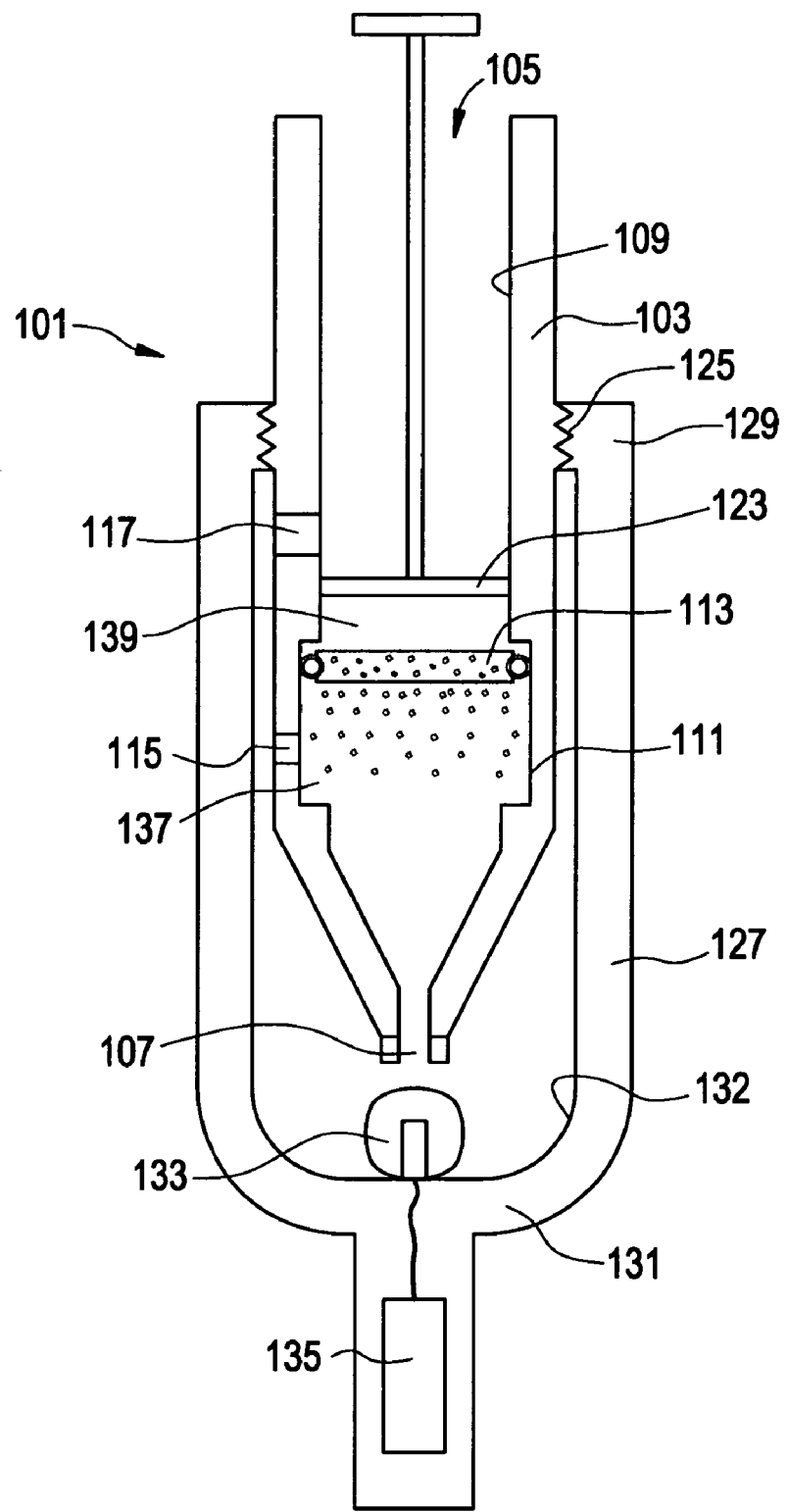
FIG. 1 is a cross-section of a syringe of the present invention having a UVB-producing unit attached thereto.

In one embodiment of the present invention, the present inventors have developed methods for treating or preventing osteolysis exploiting the characteristics of a particular cytokine, interleukin-10 (IL-10).

It is believed that IL-10 possesses a number of features that make it an attractive therapeutic agent for treating or preventing osteolysis. These include the inhibition of cytokine synthesis and the down-regulation of antigen-presenting cell function.

According to Brennan, *Rheumatology* 1999, 38, 293-7, IL-10 can induce the production of cytokine inhibitors, including the IL-1 receptor antagonist (IL-1ra) and the release of both soluble TNF receptors p55 and p75 in monocytes. Because of this utility, Brennan chartacterizes IL-10 as a 'macrophage deactivating factor'. According to Hart, *Immunology*, 1995, April 84 (4) 536-42, IL-10 and IL-4 have the capacity to downregulate both pro-inflammatory molecules TNF-a and IL-1β.

The concept of administering UVB light to therapeutically treat an auto-immune disease by producing autologous IL-10 is disclosed in U.S. Pat. No. 5,910,309 (Ullrich), the disclosure which is hereby incorporated by reference in its entirety. Shreedhar, *J. Immunol.*, 1998, 160, 3783-9, suggests that UV irradiation of keratinocytes activates a cytokine cascade as follows:

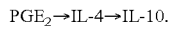

$PGE_2 \rightarrow IL-4 \rightarrow IL-10$.

Although Ullrich appreciates the benefits of IL-10, the methods of providing IL-10 disclosed by Ullrich generally concern full body irradiation producing systemic increases in IL-10. Since IL-10 has a potent immunosuppressive effect, the patient receiving such treatment would be at risk of undesired side effect of having a suppressed immune system, including an increased susceptibility towards infection.

It is noted that the autologous cells that produce IL-10 when activated by UV-B radiation (macrophages and lymphocytes) are the same cells that participate in the inflammatory response characteristic of osteolysis. Therefore, it appears that a great concentration of cells capable producing of IL-10 reside precisely within the region of undesired inflammation. Therefore, it is believed that osteolysis may be effectively treated by locally irradiating the inflamed region with UV-B light, thereby de-activating the pro-inflammatory ($Th_1$) cells in that region that are emitting pro-inflammatory cytokines and activating IL-10 emitting ($Th_2$) cells.

Accordingly, in some embodiments of the present invention, there is provided a method of treating or preventing osteolysis, comprising the steps of:

a) providing an implant having a UVB light source,
b) positioning the implant within or adjacent to an osteolytic region adjacent an orthopedic implant, and
c) activating the light source to irradiate at least a portion of the osteolytic region with an amount of UVB light sufficient to provoke a Th2 response.

In some embodiments there is provided an implant for treating osteolysis comprising:

a) a UV-B Light emitting diode (LED), and
b) an antenna in electrical connection with the LED.

Also in accordance with the present invention, there is provided a method of treating or preventing osteolysis, comprising the steps of:

a) providing a probe having a UVB light source,
b) positioning the probe within or adjacent to an osteolytic region adjacent an orthopedic implant, and
c) activating the light source to irradiate at least a portion of the osteolytic region with an amount of UVB light sufficient to provoke a Th2 response.

In use, the surgeon implants the UVB device into the joint of the patient so that the device is adjacent to a portion of the joint which is inflamed. In other embodiments, the UV device is part of the orthopedic implant. The IL-10 produced by the device will then affect the area of inflammation. However, investigators have noted systemic immunosupresive effects in animals subject to whole body (superficial) UV irradiation, and have hypothesized that the mobility of the irradiated macrophages allows them to migrate to vast regions of internal tissue. See Kang, *J. Immunol.*, 1994, 153, 5256. Accordingly, it is possible that irradiation of cells (such as macrophages) in one portion of the joint may be sufficient to arrest inflammation over a much larger region of the joint. Therefore, it is possible that the device need not be immediately adjacent the inflamed tissue, but rather may be placed at a more convenient spot for the surgeon, such as on the orthopedic implant.

In order to protect the active elements of the device from the fluids, in some embodiments, the UVB LED is encased in a casing. This casing both protects the LED components from the fluids, and also prevents the LED components from elicting a violent immune reaction. In some embodiments, the casing is made of a UVB transparent material. The UVB transparent material may be placed adjacent the LED component so that UVB light may be easily transmitted therethrough. In some embodiments, the UVB transparent casing is selected from the group consisting of silica, alumina and sapphire. In some embodiments, the light transmissible material is selected from the group consisting of a ceramic and a polymer. Suitable UVB-transmissible ceramics include alumina, silica, CaF, titania and single crystal-sapphire. Suitable light transmissible polymers are preferably selected from the group consisting of polypropylene and polyesters.

In some embodiments, it may be desirable to locate the light emitting portion of the implant at a location separate from the LED, and provide a light communication means between the two sites. The light communication means may include any of a fiber optic cable, a wave guide, a hollow tube, a liquid filled tube, and a light pipe. Such a configuration would allow a fiber optic to be located at the surface of the implant, and yet have the light source and associated components in a less sensitive region of the implant.

Shreedhar, *J. Immunol.*, 1998, 160, 3783-9 has reported that UV-induced IL-10 production is enhanced in the presence of IgG. Accordingly, in some embodiments, a distal portion of the fiber optic cable has an etched surface. Without wishing to be tied to a theory, it is believed that the etched portion will cause IgG to bind thereto. The presence of the IgG in the UV-irradiated zone of tissue will increase the rate of IL-10 production therein.

In some embodiments, the light source is situated to irradiate adjacent tissue with between about 0.02 J/cm$^2$ and 2 J/cm$^2$ energy. Without wishing to be tied to a theory, it is believed that light transmission in this energy range will be sufficient to activate the macrophages of most osteolytic tissue. Shreedhar, *J. Immunol.*, 1998, 160, 3783-9 has reported using a light dose of 0.02 J/cm$^2$ in order to activate keratinocytes to produce IL-10. Schmitt, *J. Immunology*, 2000, 165:3162-7 has reported using a dose of 1.5 J/cm$^2$. Rivas, *J. Immun*, 149, 12, 1992, 3865-71 has reported using a dose of 0.02 J/cm$^2$. Therefore, it is believed that irradiating inflamed osteolytic tissue with at least about 0.02 J/cm$^2$ of UVB radiation will induce the macrophages therein to produce and emit IL-10. In some embodiments, the light source is situated to produce an energy intensity at the cell surface of between 0.1 watts/cm$^2$ and 10 watts/cm$^2$. In some embodiments, the light source is situated to produce about 1 milliwatt/cm$^2$. This latter value has been reported by Ullrich to effectively irradiate a cell surface in an amount sufficient to produce IL-10.

In some embodiments, there is provided a first exemplary implant having an external light source. The externally based-control device has a light source for generating light within the device. The light generated by this source is transmitted through a fiber optic cable through the patient's skin to an internally-based light port provided on the proximal surface of the implant. The light port is adapted to be in light-communication with a fiber optic cable disposed upon the distal surface surface of the implant. Tynes disposed upon the distal portion of the fiber optic cable receive the light and transmit the light to the adjacent osteolytic tissue.

In other embodiments, there is provided a second exemplary UVB unit having an internal light source. An externally based-control device having an RF energy source and a transmitting antenna transmits signals to an internally-based receiving antenna provided on the prosthesis. These antennae may be electro-magnetically coupled to each other. The internal antenna sends electrical power to a light emitting diode (LED) disposed internally on the implant in response to the transmitted signal transmitted by the external antenna. The light generated by the LED travels across UVB transparent casing and into the osteolytic tissue.

In some embodiments, the prosthesis having an internal light source further contains an internal power source, such as a battery (which could be re-chargeable), which is controlled by an internal receiver and has sufficient energy stored therein to deliver electrical power to the light source in an amount sufficient to cause the desired light output.

When the implant is coupled with external energy, power can be transmitted into the internal device to re-charge the battery.

In some embodiments, the light generated by the implant is powered by wireless telemetry integrated onto or into the implant itself. The LED may comprise a radiofrequency-to-DC converter and modulator. When radiofrequency signals are emitted by the external antenna and picked up by the internal antenna, these signals are then converted by the receiver into electrical current to activate the light source of the unit.

In one embodiment, the implant may have an internal processor adapted to intermittently activate the LED.

In some embodiments, the telemetry portion of the device is provided by conventional, commercially-available components. For example, the externally-based power control device can be any conventional transmitter, preferably capable of transmitting at least about 40 milliwatts of energy to the internally-based antenna. Examples of such commercially available transmitters include those available from Microstrain, Inc. Burlington, Vt. Likewise, the internally-based power antenna can be any conventional antenna capable of producing at least about 40 milliwatts of energy in response to coupling with the externally-generated Rf signal. Examples of such commercially available antennae include those used in the Microstrain Strainlink™ device. Conventional transmitter-receiver telemetry is capable of transmitting up to about 500 milliwatts of energy to the internally-based antenna.

In some embodiments, the UVB light source has a spectral maximum in the range of the UVB components of the solar spectrum. Preferably, the light source has a spectral maximum in the range of the UVB components of the solar spectrum. Preferably, the light source has a spectral maximum in the range of less than about 320 nm, and is preferably between 280 nm and 320 nm. In some embodiments, the light source has a spectral maximum of between 280 nm and 315 nm. In some embodiments, the light source is a narrowband light source having a spectral maximum of between 311 nm and 312 nm.

In some embodiments, the light source is provided on the implant and is adapted to be permanently implanted into the patient. The advantage of the internal light source is that there is no need for further transcutaneous invasion of the patient. Rather, the internally-disposed light source is activated by either a battery disposed on the implant, or by telemetry, or both. In some embodiments of the present invention using an internal light source, the light source is provided by a bioMEMs component. In one embodiment thereof, the internal light source comprises a UVB light source, and preferably comprises an AlGaN substrate. It has been reported by Stutzmann, *Diamond and Related Materials*, 11 (2002) 886-891, that AlGaN may have future application as a biosensor. Stutzman further conducted studies on the biocompatibility of GaN, AlGaN and AlN, and found very little interaction with living cell tissue, thereby suggesting the biocompatibility of these materials.

In some embodiments, it may be advantageous to combine the autologous production of IL-10 with an administration of exogenous IL-10. The exogenous IL-10 provides the benefit of a) insuring immediate IL-10 activity, and b) possibly super-inducing the production of the autologous IL-10.

In some embodiments of the present invention, UVB irradiation causes sufficient IL-10 production to produce a local IL-10 concentration of at least 0.1 ng/ml. Shreedhar, *J. Immunol.*, 1998, 160, 3783-9, reports producing 313 pg IL-10/ml by exposing keratinocytes to 0.02 J/cm$^2$ UV light, while Kang, *J. Immunol.*, 1994, 153, 5256 reports producing 333 pg/ml in a supernatant from CD11b+ macrophages exposed to 4 MEDs of UV light.

In some embodiments of the present invention, UVB irradiation causes sufficient IL-10 production to produce a local IL-10 concentration of at least 1 ng/ml. Shreedhar, *J. Immunol.*, 1998, 160, 3783-9, reports producing about 1.7 ng/ml of IL-10 by exposing mice to 0.015 J/cm$^2$ of UV radiation and then injecting the mice with IgG.

In some embodiments, the UVB light of this invention is directed against osteolysis occurring due to wear debris (typically UHMWPE wear debris) from a hip joint prosthesis (preferably an acetabular cup). In some embodiments thereof, the acetabular cup is selected from the cups disclosed in U.S. Pat. Nos. 5,282,864; 6,017,975; and 6,228,900, the specifications of which are incorporated by reference in their entireties. In these embodiments, a fiber optic cable carrying UVB light may be placed through the proximal face of the acetabular cup via semicircular holes in the metal liner and travel through the cup to the distal hole in the cup backing, thereby providing for a local treatment of wear exiting the distal hole in the cup backing.

In some embodiments, the UVB light of this invention is directed against osteolysis occurring due to wear debris (typically UHMWPE wear debris) from a knee joint prosthesis (preferably a tibial insert upon a tibial tray).

In some embodiments, the UVB light of this invention is directed against lysis occurring due to wear debris (typically UHMWPE wear debris) from an intervertebral motion disc prosthesis (typically a cervical motion disc).

It is well known in the art that inflammation is characterized not only by the presence of macrophages, but also the presence of lymphocytes. For example, Virri, Spine, November 1, 26(21) 2311-5 reports that 17% of examined discs contained abundant T cells, 17% of examined discs contained activated T cells, 16% of examined discs contained abundant B cells, and 34% of examined discs contained abundant macrophages. Since it is also known that lymphocytes may secrete pro-inflammatory cytokines via the Th1 pathway, it is appropriate to consider the activity of these cells in osteolytic therapies.

U.S. Pat. No. 6,083,919 (Johnson) has reported co-administration of IL-10 and TGF-β in amounts effective to produce a synergistic reduction in lymphocyte activity. In one example, Johnson reports that about 0.3 ng/ml of each of IL-10 and TGF-β inhibits the activation of self-reactive T cells in autoimmune diseases from 20,000 units to less than 500 units.

Therefore, in accordance with the present invention, there is provided a method of treating osteolysis, wherein both IL-10 and TGF-β are administered periprosthetically in amounts effective to produce a synergistic reduction in lymphocyte activity.

In one embodiment of the present invention, effective amounts of TGF-β can be obtained by activation of platelet-rich plasma (PRP). Preferably, the TGF-β is administered to provided an effective concentration of at least 1 ng/ml.

In other embodiments, the TGF-β is replaced with rhGDF-5.

In some embodiments, the UVB irradiation of the osteolytic region is performed a single time. In others, it is performed multiple times. In some embodiments, it is performed about 3 times a week for several weeks.

In some embodiments, the UVB light source is situated on the orthopedic implant. In others, it is provided separately, either as a separate implant or as a probe, preferably at the time of onset of osteolysis.

In other embodiments, the present invention relates to the UVB irradiation of white blood cells in order to induce tolerance to the antigenic collagen—wear particle complexes produced by wear.

In one embodiment of the present invention, UVB-irradiated, autologous macrophages and lymphocytes are combined ex vivo with the antigenic collagen—wear particle complex and then injected into the patient near in the vicinity of a lymph node.

The UVB irradiation of the macrophages will change the character of the antigen presenting function of the macrophages from a pro-inflammatory to an anti-inflammatory character. Accordingly, when the tolerogenic macrophage engulfs an antigenic collagen—wear particle complex and presents it to B cells in the lymph node, the resulting immune response will be that of a Th2 anti-inflammatory response.

Likewise, UVB irradiation of the lymphocytes will induce a release of anti-inflammatory IL-10 therefrom. The increase in IL-10 in the region surrounding the macrophages will further polarize the immune response to an anti-inflammatory Th2 response.

Therefore, in accordance with the present invention, there is provided a method of treating osteolysis, comprising the steps of:
  a) irradiating autologous macrophages with UVB light to cause tolerance therein, and
  b) combining the tolerized macrophages with an antigenic collagen—wear particle complex to form a mixture, and
  c) injecting the mixture into the patient.

The UVB irradiated cells should behave in a very tolerogenic, anti-inflammatory manner and produce systemic tolerance to the antigens they encounter. In particular, the antigen-presenting function of macrophages will become tolerogenic, while the lymphocytes should begin to emit IL-10.

In preferred embodiments, this procedure once a week for about 4 weeks, thereby provoking a desirable, long-lasting tolerance of the antigenic collagen—wear particle complex.

In preferred embodiments, white blood cell (WBC) tolerance is achieved by a procedure comprising the steps of:
  a) drawing blood from the patient suffering from osteolysis,
  b) centrifuging the blood to isolate the lymphocytes and macrophages therein,
  c) withdrawing the lymphocytes and macrophages from the centrifuged blood,
  d) UVB irradiating the lymphocytes and macrophages to cause tolerance.

In preferred embodiments, a physiologic fluid containing viable WBCs is obtained from the patient. Preferably, the physiologic fluid is whole blood. Whole blood contains monocytes and lymphocytes and is easily obtainable from the patient. More preferably, the obtained whole blood is then fractionated by a conventional procedure (such as centrifugation or filtration) to obtain a selected portion of whole blood.

In some embodiments, the selected portion comprises the buffy coat fraction of whole blood. The buffy coat typically comprises about 5-10 vol % of whole blood. Utilization of the buffy coat in the present invention is desirable because it contains a concentrated amount of monocytes and lymphocytes. Typically, the cellular concentration in the buffy coat will be on the order of 10-20 fold over whole blood. In some embodiments, a fraction of the buffy coat may be used.

Preferably, white blood cells are selected as the viable cells are the present invention. These cells are easily obtained in a concentrated form from the simple centrifugation of a small amount of blood taken from the patient. More preferably, the monocyte fraction of white blood cells is selected as the viable cells of the present invention, as monocytes have been shown to become tolerogenic upon irradiation by UVB light. In other embodiments, the white blood cell fraction is lymphocytes.

In one embodiment, filtration and dewatering of blood is carried out in accordance with U.S. Pat. No. 5,733,545 (Hood) to obtain a buffy coat having about $14 \times 10^6$ monocytes/ml.

Once the WBCs are tolerized and the collagen—wear particle complexes are obtained, the two are combined ex vivo and then re-injected back into the patient, preferably in the vicinity of a lymph node associated with the osteolytic joint.

In general, "Wear Particles" includes a) actual wear particles produced from the articulation of two surfaces, and b) particles having a composition and particle size distribution substantially similar to actual wear particles produced from the articulation of two surfaces. For example, "Wear Particles" includes UHMWPE particles produced from a physiologic articulation of a UHMWPE acetabular cup and a prosthetic femoral head, and b) particles having a composition and particle size distribution substantially similar to actual wear particles produced from the physiologic articulation of a UHMWPE acetabular cup and a prosthetic femoral head so as to cause an osteolytic response.

In some embodiments, the Wear Particles are titanium or a titanium alloy. This will allow immunization for Wear Particles emanating from articulation surfaces comprising titanium. In some embodiments, the Wear Particles are cobalt-chrome. This will allow immunization for Wear Particles emanating from articulation surfaces comprising cobalt-chrome. In some embodiments, the Wear Particles are UHMWPE. This will allow immunization for Wear Particles emanating from articulation surfaces comprising UHMWPE, such as those in UHMWPE acetabular cups or tibial components. In some embodiments, the Wear Particles are PMMA. This will allow immunization for particles emanating from cemented surfaces.

In some embodiments wherein the articulating implant has a UHMWPE articulating surface opposing a metal articulating surface, the Wear Particles may be a mixture comprising metal particles and UHMWPE particles. In some embodiments, the mixture comprises about 75 wt % UHMWPE particles and about 25 wt % metal particles.

Generally, the Wear Particles of the present invention are characterized by a $D_{50}$ particle size of between 0.1 μm and 10 μm, preferably between 0.3 μm and 5 μm, more preferably between 0.5 μm and 3 μm. Preferably, the Wear Particles are provided in a particle size distribution substantially corresponding to the particle size distribution that are produced at the articulation interface of the prosthetic component during wear and then targeted for attack by the immune system. For example, in one embodiment, the antigen is 1-2 μm UHMWPE particles.

Generally, the Wear Particles of the present invention are present in a concentration of about $10^7$ particles/cc to $10^{13}$ particles/cc.

The amount of Wear Particles in the formulation of the present invention should be sufficient to allow antigen presenting cells to provide the proper signaling to T cells to activate a Th2 immune response, but not so much as to cause an exaggerated immune response. For example, it is believed that, in some embodiments, the amount of Wear Particles in the formulation should be between about 1% and 10% of the amount of wear particles generated over a one month's span by the prosthesis with which the formulation will be used.

In some embodiments, collagen is used to form a collagen-Wear Particle complex. Collagen typically has a hydrophobic tail. It is believed that this tail of the added collagen will complex with the Wear Particles in the same manner that the patient's collagen complexes with Wear Particles produced from a prosthesis, and thereby change the presentation of the collagen to the immune system to provide novel epitopes to the immune system.

In some embodiments, the collagen is provided in a soluble form. In some embodiments, the collagen is provided in a fibrillar form. The fibrillar form is preferred because it can be used in a slurry and thereby help keep the Wear Particles localized.

In some embodiments, the collagen is recombinant human collagen. Providing human collagen will minimize the variances between the added collagen and the collagen of the patient, and so will allow the formulation to mimic as closely as possible the natural complexation that typically occurs during osteolysis.

Preferably, the collagen is selected from the group consisting of types I, type II, type IV and type V collagen. Type II collagen is particularly preferred.

In some embodiments, antigen presenting cells are added to the formulation. In some embodiments, thereof concentrated, immature dendritic cells may be added to the formulation in order to enhance the antigen presenting function. Preferably, the dendritic cells are provided by the patient's blood or bone marrow, and may be concentrated by conventional methods, including the centrifugal elutriation procedure disclosed in Ossevoort, *J. Immunological Methods*, 155, 1992, 101-111.

In other embodiments, concentrated macrophages may be added (from a buffy coat) in order to enhance the antigen presenting function. Preferably, the macrophages are provided by the patient's blood or bone marrow, and may be concentrated by conventional methods, including the centrifugation.

TGF-β can be added to help convert the immature dendritic cells to DC2 cells and to drive the polarization of the immune response to Th2. Liu, *Nature Immunology*, 2(7), July 2001 585-589, and King, *Immunity*, 8, May 1998, 601-613. Therefore, in some embodiments, the formulation additionally comprises an effective amount of TGF-β. In some embodiments thereof, the TGF-β is obtained from platelets from the patient's blood. In other embodiments thereof, the TGF-β is exogenous.

In some embodiments, the tolerized WBCs and the collagen—wear particle complexes are combined ex vivo and then re-injected into the patient in the vicinity of a lymph node. Preferably, the lymph node is one that serves the osteolytic joint.

In some embodiments, the tolerized WBCs and collagen—Wear Particle complexes are combined ex vivo and then re-injected into the patient in the vicinity of mucosa-associated lymphoid tissue (MALT). Mucosal administration of certain antigens causes suppressor T-cells to be induced in mucosa-associated lymphoid tissue (MALT). These antigen-specific suppressor T-cells are released in the blood or lymphatic tissue and then migrate to the organ or tissue afflicted by the autoimmune disease (which has a high concentrated of the antigen). Once they have arrived at their intended target, these suppressor T-cells mediate the release of immunosuppressive cytokines such as transforming growth factor β (TGF-β), IL-4 and/or IL-10 and thereby suppress autoimmune attack of the afflicted organ or tissue.

In more detail, the mechanism of bystander suppression is as follows: After a tissue-specific bystander antigen is mucosally administered, it passes to local lymph tissue (such as Peyers Patches in the gut), which contain T cells and B cells. These cells, are in turn in communication with the immune system, including the spleen and lymph nodes. The result is that suppressor (CD8+) T-cells are induced and recruited to the area of autoimmune attack, where they cause the release of TGF-β, IL-4 and IL-10, which can non-specifically down-regulate the B-cells as well as the activated CD4+T-cells directed against the mammal's own tissues. Despite the non-specific nature of the activity of these cytokines, the resulting tolerance is specific for the autoimmune disease by virtue of the fact that the antigen is specific for the tissue under attack and suppresses the immune cells that are found at or near the tissue being damaged.

TGF-B is an anti-inflammatory cytokine that helps polarize the immune response towards a Th2 phenotype. IL-4 and IL-10 are also antigen-nonspecific immunoregulatory cytokines. IL-4 in particular enhances Th2 response, i.e., acts on T-cell precursors and causes them to differentiate preferentially into Th2 cells at the expense of Th1 responses. IL-4 also indirectly inhibits Th1 exacerbation. IL-10 is a direct inhibitor of Th1 responses. After orally tolerizing mammals afflicted with autoimmune disease conditions with bystander antigens, increased levels of TGF-β, IL-4 and IL-10 are observed at the locus of autoimmune attack. Chen, Y. et al., Science, 265:1237-1240, 1994.

The action of these cytokines is not specific for the antigen triggering the suppressor cells that release them, even though these suppressor T-cells release these cytokines only when triggered by the mucosally-administered antigen. However, because mucosal tolerization with the antigen only causes the release of these cytokines in the vicinity of autoimmune attack, no systemic immunosuppression ensues. Recruitment of the suppressor T-cells to a locus where cells contributing to the autoimmune destruction are concentrated allows for the release of these suppressive cytokines in the vicinity of the disease-causing cells and suppresses (i.e. shuts down) these cells. The ability of these immunosuppressive cytokines to suppress these "destructive" cells is independent of the antigen for which the destructive cells may be specific.

In some embodiments, the tolerized WBCs and collagen—Wear Particle complexes are combined ex vivo and then re-injected into the patient in the vicinity of the nasal-associated lymphoid tissue (NALT)

U.S. Pat. No. 6,645,504 ("Weiner I") and U.S. Pat. No. 5,935,577 ("Weiner II") each discloses that certain synergists can be co-administered along with the antigen to enhance the effectiveness of the tolerance-promoting treatment. Particularly, noted is the use of IL-4; IL-10; bacterial lipopolysaccharides; immunoregulatory lipoproteins; and cholera toxin β-chain (CTB). Therefore, in some embodiments, a synergist selected from the group consisting of IL-4; IL-10; bacterial lipopolysaccharides; immunoregulatory lipoproteins; and cholera toxin β-chain (CTB) can be co-administered along with the antigen to enhance the effectiveness of the tolerance-promoting treatment.

Now referring to FIG. 1, there is provided a syringe 101 adapted for tolerizing the WBCs of the present invention. This syringe is adapted to receive concentrated cells, dewater the cells, receive compounds such as collagen-Wear Particle complexes, receive UVB light, and finally deliver the tolerized cells to the patient.

The syringe comprises a barrel 103 having an inner wall 109, a proximal open end 105 and a distal open end 107. A recess 111 is provided in a portion of the inner wall in order to accommodate axial sliding of moveable filter 113. The syringe further has side ports 115 and 117 having gaskets 119 and 121 therein. The syringe further include a plunger having a distal plug 123, and a threaded portion 125 adapted for threadable connection to a UVB source.

The apparatus as shown further includes a UVB source 127 adapted for connection to the syringe. The purpose of the UVB source is to reliably produce an appropriate dose of UVB radiation to the WBC cells. The UVB source has a threaded end 129 adapted for threadable connection with the corresponding thread on the outer surface of the syringe. The UVB source has a closed end 131 having an inner surface 132 having a cup shape which houses a UVB light 133 connected to an energy source 135. The inner surface is preferably made of a reflective material to direct the UVB light towards the WBCs, while cup shape of the inner surface also directs the UVB light towards the WBCs In use, the clinician adds the concentrated cells (preferably, at least PBMCs) to the chamber 137 defined by the syringe barrel and filter. Next, the collagen—Wear Particle complexes are added to the chamber, optionally through port 115. Next, the UVB source is threaded onto the syringe and the UVB source is activated to irradiate the cells with an effective amount of UVB light. Next, plunger is partially withdrawn from the barrel, thereby creating a vacuum and drawings fluid from the chamber 137 into space 139. A needle is then inserted into space 139 through port 117 in order to remove the withdrawn fluid.

In some embodiments, cryoprecipitated fibrinogen and thrombin are added to the chamber through port 115 in order to begin the clotting process, which keeps the cells localized.

Lastly, the plunger is advanced so that the contents of the chamber 37 are injected into the vicinity of a lymph node.

EXAMPLE I

This prophetic example describes a typical method of the present invention.

First, about 20 cc of blood is taken from the patient. Now referring to FIG. 2, the blood is placed in a centrifugation container 1 adapted for centrifugation and having a side wall 2.

Now referring to FIG. 3, the blood is centrifuged to produce centrigued blood fractions including red blood cells 11, platelets 13, buffy coat 15 and platelet poor plasma 17.

Now referring to FIG. 4, a syringe 21 having a barrel 23 containing a fluid 31 comprising collagen—Wear Particle complexes and a needle 25 is provided. The centrifugation container has a plurality of side ports 3 having puncturable gaskets 5 therein. The clinician inserts the distal end 27 of the needle through the lowest gasket in the buffy coat portion of the fractionated blood.

Now referring to FIG. 5, the clinician pulls back upon the plunger 29. The vacuum created by withdrawl of the plunger causes the buffy coat fluid to enter the barrel of the syringe, thereby mixing with the collagen—Wear Particle complexes and producing a collagen—wear particle complex—rich buffy coat fluid 41.

Next, the clinician attaches the UVB source and provides an effective amount of UVB light to the WBCs.

After mixing and irradiation, the clinician then waits several hours in order for the collagen—wear particle complexes to interact with the tolerized monocytes in the fluid.

Next, the physician partially withdraws the plunger and dewaters the formulation.

Next, the clinician receives the syringe having the inventive composition of the present invention. This syringe has a small gauge needle, typically a 22 or 24 gauge needle. The barrel of the syringe contains the formulation of the present invention.

Finally, and now referring to FIG. 6, the clincian depresses the plunger of the syringe, thereby injecting an effective amount of the formulation comprising tolerized cells and collagen—wear particle complex into a region 53 in the vicinity of a lymph node 51, or into the lymph node 51 itself.

We claim:
1. A method of treating or preventing osteolysis, comprising the steps of:
  a) providing a probe having a UVB light source,
  b) positioning the probe within or adjacent to an osteolytic region adjacent an orthopedic implant, and
  c) activating the light source to irradiate at least a portion of the osteolytic region with an amount of UVB light sufficient to provoke a tolerogenic response.

2. The method of claim 1 wherein the UVB light source is situated to irradiate at least a portion of the osteolytic region with between about 0.02 J/cm$^2$ and 2 J/cm$^2$ UVB energy.

3. The method of claim 1 wherein the UVB light source is a narrowband light source having a spectral maximum of between 311 nm and 312 nm.

4. The method of claim 1 wherein the orthopedic implant is a hip joint prosthesis.

5. The method of claim 1 wherein the orthopedic implant is a knee joint prosthesis.

6. The method of claim 1 wherein the UVB irradiation of the osteolytic region produces a local IL-10 concentration of at least 0.1 ng/ml.

7. The method of claim 1 further comprising the step of:
   d) administering TGF-β to the osteolytic region in amounts effective to produce a synergistic reduction in lymphocyte activity.

8. A method of treating osteolysis in a patient, comprising the steps of:
   a) irradiating autologous white blood cells with UVB light to cause tolerance therein, and
   b) combining the tolerized white blood cells with a collagen-wear particle complexes to form a mixture, and
   c) injecting the mixture into the patient in the vicinity of a lymph node.

9. The method of claim 8 wherein the white blood cells comprise monocytes.

10. The method of claim 9 wherein the monocytes are present in a concentration of at least $10^6$/cc.

11. The method of claim 8 wherein the white blood cells comprise lymphocytes.

12. The method of claim 8 wherein the white blood cells comprise dendritic cells.

13. The method of claim 8 wherein the UVB light is narrowband UVB.

14. The method of claim 8 wherein the UVB light has a maximum emission of 311-312 nm.

15. The method of claim 8 wherein the UVB light irradiates the cells with between about 0.02 J/cm$^2$ and 20 J/cm$^2$ energy.

\* \* \* \* \*